(12) United States Patent
Dutkiewicz et al.

(10) Patent No.: US 6,562,742 B2
(45) Date of Patent: May 13, 2003

(54) HIGH-PERFORMANCE ABSORBENT STRUCTURE

(75) Inventors: Jacek K. Dutkiewicz, Cordova, TN (US); Sanjay Wahal, Cordova, TN (US); Ryan K. Hood, Memphis, TN (US); John P. Erspamer, Lakeland, TN (US); Brian E. Boehmer, Bartlett, TN (US)

(73) Assignee: BKI Holding Corporation, Wilmington, DE (US)

( * ) Notice: Subject to any disclaimer, the term of this patent is extended or adjusted under 35 U.S.C. 154(b) by 0 days.

(21) Appl. No.: 09/475,850

(22) Filed: Dec. 30, 1999

(65) Prior Publication Data

US 2003/0012919 A1 Jan. 16, 2003

Related U.S. Application Data

(60) Provisional application No. 60/116,036, filed on Jan. 11, 1999.

(51) Int. Cl.⁷ .............................. B32B 5/18; B32B 5/24
(52) U.S. Cl. ...................... 442/375; 442/381; 442/393; 604/378; 604/358; 604/368
(58) Field of Search .................................. 604/378, 358, 604/368; 442/375, 381, 393

(56) References Cited

U.S. PATENT DOCUMENTS

| | | | |
|---|---|---|---|
| 4,540,625 A | 9/1985 | Sherwood | 428/283 |
| 4,604,313 A | 8/1986 | McFarland et al. | 428/172 |
| 4,699,823 A | 10/1987 | Kellenberger et al. | 428/219 |
| 4,868,032 A | 9/1989 | Eian et al. | 428/198 |
| 4,902,559 A | 2/1990 | Eschwey et al. | 428/224 |
| 4,950,531 A | 8/1990 | Radwanski et al. | 428/284 |
| 5,043,206 A | 8/1991 | Ternstrom | 428/218 |
| 5,043,209 A | 8/1991 | Boisse et al. | 428/233 |
| 5,087,506 A | 2/1992 | Palumbo | 428/194 |
| 5,135,787 A | 8/1992 | Bair | 428/36.1 |
| 5,143,779 A | 9/1992 | Newkirk et al. | 428/218 |
| 5,230,959 A | 7/1993 | Young, Sr. et al. | 428/372 |
| 5,246,772 A | 9/1993 | Manning | 428/287 |
| 5,262,223 A | 11/1993 | Palumbo et al. | 428/195 |
| 5,271,987 A | 12/1993 | Iskra | 428/192 |
| 5,294,478 A | 3/1994 | Wanek et al. | 428/218 |
| 5,294,483 A | 3/1994 | Beavers et al. | 428/336 |
| 5,308,896 A | 5/1994 | Hansen et al. | 524/13 |
| 5,328,759 A | 7/1994 | McCormack et al. | 428/283 |

(List continued on next page.)

OTHER PUBLICATIONS

U.S. patent application Ser. No. 09/232,783, Baer et al., filed Jan. 19, 1999.

*Primary Examiner*—Daniel Zirker
*Assistant Examiner*—Victor S Chang
(74) *Attorney, Agent, or Firm*—Darby & Darby

(57) ABSTRACT

Disclosed is an absorbent structure having wet integrity higher than about 4.0 kN/gsm, softness higher than 8.0/J, pliability higher than about 70/N, and providing a substantially dry liquid-accepting surface after receiving a quantity of liquid. The structure includes an upper ply having an upper fluid receiving surface and a lower surface and including (i) a top stratum including synthetic matrix fibers bonded with a binder, the matrix fibers having length from about 2 to about 15 mm; (ii) a middle stratum in fluid communication with the top stratum, the middle stratum including natural fibers, superabsorbent particles and a binder; and (iii) a bottom stratum in fluid communication with the middle stratum, the bottom stratum including natural fibers and a binder. The structure also includes a lower ply in fluid communication with the upper ply, the lower ply having an upper surface and a lower surface and including at least one stratum including natural fibers, superabsorbent polymer particles, and a binder, wherein the lower surface of the upper ply has a surface area less than about 80% of the upper surface area of the lower ply.

79 Claims, 2 Drawing Sheets

U.S. PATENT DOCUMENTS

| | | | |
|---|---|---|---|
| 5,350,370 A | 9/1994 | Jackson et al. | 604/367 |
| 5,360,420 A | 11/1994 | Cook et al. | 604/378 |
| 5,387,208 A * | 2/1995 | Ashton et al. | 604/378 |
| 5,409,768 A | 4/1995 | Dickenson et al. | 428/283 |
| 5,432,000 A | 7/1995 | Young, Sr. et al. | 428/372 |
| 5,447,977 A | 9/1995 | Hansen et al. | 524/13 |
| 5,453,314 A | 9/1995 | Collier et al. | 428/198 |
| 5,466,513 A | 11/1995 | Wanek et al. | 428/218 |
| 5,490,846 A | 2/1996 | Ellis et al. | 604/366 |
| 5,516,569 A | 5/1996 | Veith et al. | 428/68 |
| 5,516,585 A | 5/1996 | Young, Sr. et al. | 428/372 |
| 5,522,810 A | 6/1996 | Allen, Jr. et al. | 604/366 |
| 5,571,618 A | 11/1996 | Hansen et al. | 428/359 |
| 5,601,542 A | 2/1997 | Melius et al. | 604/368 |
| 5,614,570 A | 3/1997 | Hansen et al. | 524/13 |
| 5,628,736 A | 5/1997 | Thompson | 604/366 |
| 5,637,106 A | 6/1997 | Mitchell et al. | 604/368 |
| 5,645,542 A | 7/1997 | Anjur et al. | 604/368 |
| 5,681,300 A | 10/1997 | Ahr et al. | 604/367 |
| 5,763,331 A | 6/1998 | Demhartner | 442/68 |
| 5,801,107 A | 9/1998 | Everhart et al. | 442/408 |
| 5,821,179 A * | 10/1998 | Masaki | 442/375 |
| 5,833,678 A | 11/1998 | Ashton et al. | 604/378 |
| 5,849,405 A | 12/1998 | Wang et al. | 428/304.4 |
| 5,866,242 A | 2/1999 | Tan et al. | 428/219 |
| 5,877,097 A | 3/1999 | West et al. | 442/327 |
| 5,906,602 A | 5/1999 | Weber et al. | 604/385.1 |
| 5,916,670 A | 6/1999 | Tan et al. | 428/219 |
| 5,922,163 A | 7/1999 | Helynranta et al. | 156/296 |
| 5,928,209 A | 7/1999 | Bodford et al. | 604/370 |

\* cited by examiner

HIGH-PERFORMANCE ABSORBENT STRUCTURE

CROSS-REFERENCE TO RELATED APPLICATIONS

This application claims priority under 35 U.S.C. §119, based on U.S. Provisional Application Ser. No. 60/116,036, filed Jan. 11, 1999, the entire disclosure of which is hereby incorporated by reference.

FIELD OF THE INVENTION

The present invention relates to high-capacity, thin and highly conformable absorbent structures, useful in absorbent articles including baby diapers, adult incontinence products, sanitary napkins and the like. More particularly, the present invention relates to absorbent structures containing matrix fibers, binders and superabsorbent polymers, the structure having an x-directional fluid storage profile.

BACKGROUND OF THE INVENTION

Absorbent structures are important in a wide range of disposable absorbent articles including baby diapers, adult incontinence products, sanitary napkins and the like.

These and other absorbent articles are generally provided with an absorbent core to receive and retain body liquids. The absorbent core is usually sandwiched between a liquid pervious topsheet, whose function is to allow the passage of fluid to the core and a liquid impervious backsheet whose function is to contain the fluid and to prevent it from passing through the absorbent article to the garment of the wearer of the absorbent article.

An absorbent core for diapers and adult incontinence pads frequently includes fibrous batts or webs constructed of defiberized, loose, fluffed, hydrophilic, cellulosic fibers. The core may also include superabsorbent polymer ("SAP") particles, granules, flakes or fibers (collectively "particles").

In recent years, market demand for an increasingly thinner and more comfortable absorbent article has increased. Such an article may be obtained by decreasing the thickness of the diaper core, by increasing the amount of SAP particles, and by calendaring or pressing the core to reduce caliper and hence, increase density.

However, higher density cores do not absorb liquid as rapidly as lower density cores because densification of the core results in a smaller effective pore size. Accordingly, to maintain suitable liquid absorption, it is necessary to provide a low-density layer having a larger pore size above the high-density absorbent core to increase the rate of uptake of liquid discharged onto the absorbent article. The low-density layer is typically referred to as an acquisition layer. Multiple layer absorbent core designs involve a more complicated manufacturing process.

The storage layer portion of a disposable diaper for example, is generally formed in place, during the converting process, from loose, fluffed cellulose. Such cellulose material is generally not available in preformed sheet form because it exhibits insufficient web strength, owing to its lack of interfiber bonding or entanglement, to be unwound or unfestooned directly onto and handled in absorbent pad-making equipment.

Some absorbent articles such as ultra-thin feminine napkins are generally produced from roll-goods based nonwoven material. Such a roll of preformed absorbent core material is unwound directly as feedstock into the absorbent article converting equipment without the defiberization step normally required for fluff-based products, such as diapers and incontinence pads. The nonwoven web is typically bonded or consolidated in a fashion that gives it sufficient strength to be handled during the converting process. Absorbent structures made from such nonwoven webs may also contain SAP particles. However, these absorbent structures are often inefficient in cases where a demand is for acquisition and absorption of high amounts or a surge of body fluids. In these cases, a single sheet absorbent material often is not sufficient to fully utilize the absorbent core because the liquid is not distributed in the structure along the length of the absorbent core. As a result, regions of the absorbent core remain unused.

The web consolidation mechanism used in the roll-goods approach to making preformed cores provides strength and dimensional stability to the web. Such mechanisms include latex bonding, bonding with thermoplastic or bicomponent fibers or thermoplastic powders, hydroentanglement, needlepunching, carding or the like. However, such bonded materials provide a relatively stiff core which often does not conform well to the shape of the human body, especially in those situations where there is a demand for good fit to acquire and contain high volumes of body fluids.

Pliability and softness of the absorbent core are necessary to ensure that the absorbent core can easily conform itself to the shape of the human body or to the shape of a component (for example another absorbent ply) of the absorbent article adjacent to it. This in turn prevents the formation of gaps and channels between the absorbent article and the human body or between various parts of the absorbent article, which might otherwise cause undesired leaks in the absorbent article.

Integrity of the absorbent core is necessary to ensure that the absorbent core does not deform and exhibit discontinuities during its use by a consumer. Such deformations and discontinuities can lead to a decrease in overall absorbency and capacity, and an increase in undesired leakages. Prior absorbent structures have been deficient in one or more of pliability, integrity, profiled absorbency and capacity. For example, a conventional (fluff pulp) core has good conformability because of its high pliability and softness but at the same time it may disintegrate easily during use, due to its poor integrity. As another example, certain bonded cores, such as airlaid cores made from cellulose fluff pulp densified to greater than 0.35 g/cc have good dry integrity, but have poor wet integrity and poor conformablity.

The absorbent materials described herein exhibit a superior combination of x-directional storage profile, conformability and integrity. This combination provides improved fluid acquisition and containment as well as increased comfort and reduced leakage potential. Further, the improved integrity of the disclosed absorbent materials reduces the risk of deformation of the absorbent material and better protects the surface of the skin of the user from exposure to liquid.

SUMMARY OF THE INVENTION

The present invention relates to an absorbent structure having wet integrity higher than about 4.0 kN/gsm, softness higher than 8.0/J, pliability higher than about 70/N, and providing a substantially dry liquid-accepting surface after receiving a quantity of liquid. The structure includes an upper ply having an upper fluid receiving surface and a lower surface and including a top stratum including synthetic matrix fibers bonded with a binder, the matrix fibers having length from about 2 to about 15 mm; a middle stratum in fluid communication with the top stratum, the middle stratum including natural fibers, superabsorbent particles and a binder; and a bottom stratum in fluid communication with the middle stratum, the bottom stratum including natural fibers and a binder. The structure also includes a lower ply in fluid communication with the upper ply, the lower ply having an upper surface and a lower surface and including at least one stratum including natural fibers, superabsorbent polymer particles, and a binder, wherein the lower surface of the upper ply has a surface area less than about 80% of the upper surface area of the lower ply.

DETAILED DESCRIPTION OF THE INVENTION

All references cited in this application are hereby fully incorporated by reference. In case of conflict in terminology, the present disclosure controls.

Figure 1A:
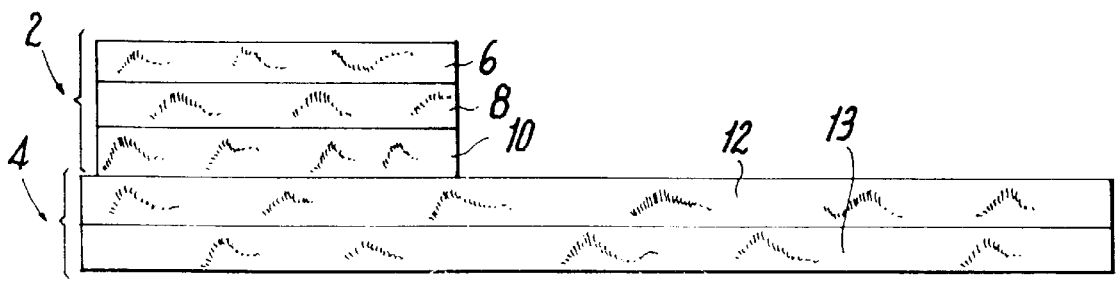
FIGS. 1a–1d depict an absorbent structure of the invention comprising an upper absorbent ply and a lower absorbent ply.

The present invention includes an absorbent structure of at least two plies of bonded absorbent material, wherein the plies are in fluid communication with each other. With reference to FIG. 1a, the structure includes: (a) a shorter, upper ply 2 having three strata 6, 8 and 10; and (b) a longer, lower absorbent ply 4. In general, the surface area of the bottom surface of upper ply 2 is less than 80% of the surface area of the upper surface of lower ply 4. This arrangement has an advantage over single-ply core structures by allowing for better containment and usage of the absorbent material during use of the absorbent article by the user.

Figure 1B:
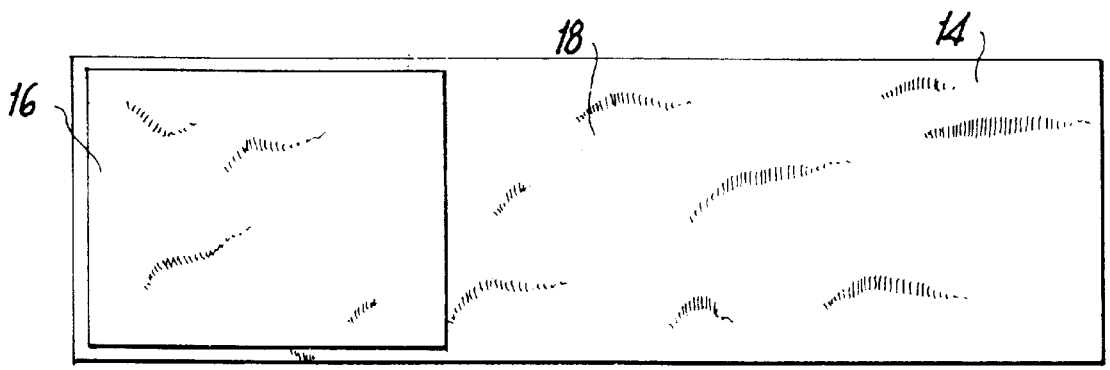

With reference to FIG. 1b, the advantage obtained by providing a two ply structure as described above, is that the fluid discharge from the human body occurs mainly over the frontal 16 and central 18 region of the absorbent core. The present invention places more of the absorbent capacity in the region where the liquid discharge insults the core. Further, the overall density of upper ply 2 is lower than the overall density of lower ply 4. This difference in densities allows for improved fluid acquisition and rewet performance since liquid is drawn from the upper ply to the lower ply due to the capillary tension gradient between the plies.

Both the upper ply and the lower ply contain binders and SAP particles. In general, the upper ply contains a higher concentration of SAP particles than the lower ply. The lower ply contains at least 30% SAP particles by weight of the lower ply. A high concentration of SAP particles provides high absorbent capacity and liquid retention within the absorbent structure. On the other hand, a lower concentration of SAP particles in the upper ply is advantageous, because gel blocking (which would lead to the inhibition of fluid flow downward to the lower ply) in this part of the absorbent structure may be avoided.

Figure 1C:
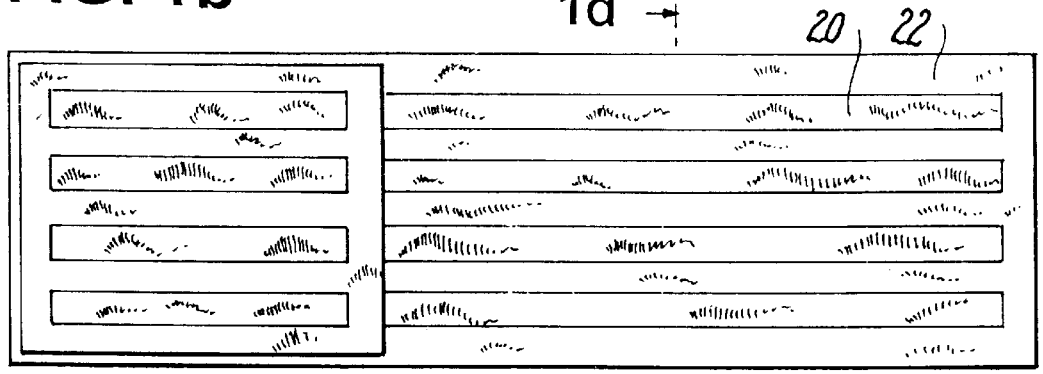
Figure 1D:
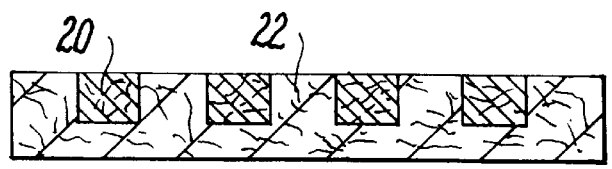

In the present invention, the SAP particles may be dispersed homogeneously within the matrix of fibers and binders. Alternatively, the SAP particles may be placed in discrete locations or zones within the structure. For example, with reference to FIGS. 1c and 1d the SAP particles may be placed in narrow lanes 20 along the absorbent core. The lanes of SAP particles are then separated by lanes of fibers 22 bonded with a binder. Such a discrete placement of SAP particles allows for better containment of the particles, facilitates flow of liquid in the Z-direction, because of the presence of areas with little or no SAP, and allows for easier flow and wicking of the fluid along the length of the core (x-direction). The areas with little or no SAP particles may be additionally densified to improve integrity and create higher capillary tension within smaller pores. Preferably, such densification takes place along the length of the absorbent structure. The pliability of such a material can thus be maintained, particularly in the y-direction (across the core).

With reference to FIG. 1a, a schematic cross-section of a preferred absorbent structure of the present invention is shown. The absorbent structure includes upper ply 2 and lower ply 4. Upper ply 2 includes three strata 6, 8 and 10 and is preferably made as a unitary airlaid structure. Upper stratum 6 is a low density acquisition layer including from between 50 to 99% by weight of wettable synthetic fibers, preferably from 75 to 90% synthetic fibers, the balance of the stratum being binder material. Due to its relatively low density, large pore size, and lower wettability than that of the layers below, top stratum 6 has essentially no aqueous liquid wicking capability. Fluid is easily wicked from it downward to the more wettable and smaller-pore, higher density strata below. Top stratum 6 includes synthetic fibers having a thickness of from 2 to 30 denier, preferably of from 6 to 15 denier. The synthetic fibers have a length of from 2 to 15 mm, preferably of from 4 to 12 mm. Optionally, the fibers may be crimped and may have a variety of cross-sectional shapes. Top stratum 8 of upper ply 2 has a basis weight of from 20 to 120 gsm (grams per square meter), preferably of from 30 to 60 gsm.

Middle stratum 8 of upper ply 2 is composed predominantly of natural fibers and also contains SAP particles. The content of SAP particles in this stratum is from 5 to 60% by weight of upper ply 2, preferably from 20 to 40% by weight of the upper ply. The basis weight of the middle stratum of the upper ply is from 50 to 1000 gsm (grams per square meter), preferably from 80 to 300 gsm. The middle stratum of the upper ply may be bonded with any suitable type of binder. Preferably, the binder is a bicomponent thermoplastic fiber, present in middle stratum 8 an amount of from 1 to 15% of the basis weight of the middle stratum and preferably from 5 to 10%.

Bottom stratum 10 of upper ply 2 includes bonded, natural fibers. This layer may be for example a wet-laid cellulose tissue bonded with binders typically used in papermaking processes. Optionally, this tissue may also be impregnated for example with one or more heat-activated binders, such as bicomponent binder fibers, which would be activated during the web curing process and would then bond the tissue together with the strata above it. The bottom stratum of the upper ply may also be formed during the formation of the upper ply, for example as a bonded airlaid layer. Any suitable binder may be used to bind stratum 10. If, for example, a binder fiber is employed for this purpose, it is present in an amount of from 3 to 15% of the basis weight of bottom stratum 10, and preferably from 5 to 10%. Other binders, such as latex-based binders or water-dispersible bonding agents used commonly in wet papermaking processes are also suitable. Stratum 10 has a basis weight of from 10 to 200 gsm, preferably from 15 to 90 gsm.

Lower absorbent ply 4 is a bonded structure of natural fibers and SAP particles. In general, the amount (in weight %) of SAP particles in lower ply 4 is higher than the amount of SAP particles in upper ply 2. The lower ply contains from 30 to 80% SAP particles by weight, and preferably from 40 to 60%.

Optionally, lower ply 4 may contain a top stratum 12, including bonded natural fibers for better containment of SAP particles in the stratum 13 or strata below it. Any suitable binder can be used to bond the structure of the lower ply. If, for example, a binder fiber is used, it is present in an amount of from 1 to 8% by weight of the lower ply, preferably from 2 to 5%.

In general, lower ply 4 has a higher overall density than the overall density of upper ply 2. The density of the lower ply may be from 0.1 to 0.35 g/cc (grams per cubic centimeter), preferably from 0.15 to 0.25 g/cc. Densities higher than 0.35 g/cc are undesirable due to reduced conformability found with such dense structures. The basis weight of the lower ply may range from 100 to 1000 gsm, preferably from 150 to 400 gsm.

The absorbent structure of the invention can be made by various forming methods and by using various raw materials such as natural and synthetic fibers, various types of SAP particles, and different kinds of binders, including fibers, powders or liquids.

Examples of the types of natural fibers which can be used in the present invention include: fluffed cellulose fibers prepared from cotton, softwood and/or hardwood pulps, straw, keaf fibers, cellulose fibers modified by chemical, mechanical and/or thermal treatments, keratin fibers such as fibers obtained from feathers, as well as man-made staple fibers made with natural polymers such as cellulose, chitin, and keratin. Examples of suitable synthetic matrix fibers include polyethylene, polypropylene, polyester, including polyester terephthalate (PET), polyamide, cellulose acetate and rayon fibers. Certain hydrophobic synthetic fibers, such as polyolefins, should be surface treated with surfactant to improve wettability.

U.S. Pat. Nos. 5,147,343; 5,378,528; 5,795,439; 5,807,916; and 5,849,211, which describe various superabsorbent polymers and methods of manufacture are hereby incorporated by reference. Examples of the types of SAP particles which may be used in this invention, include superabsorbent polymers in their particulate form such as irregular granules, spherical particles, staple fibers and other elongated particles. The term "superabsorbent polymer" or "SAP" refers to a normally water-soluble polymer, which has been cross-linked. There are known methods of making water-soluble polymers such as carboxylic polyelectrolytes to create hydrogel-forming materials, now commonly referred to as superabsorbents or SAPs, and it is well known to use such materials to enhance the absorbency of disposable absorbent articles. There are also known methods of crosslinking carboxylated polyelectrolytes to obtain superabsorbent polymers. SAP particles useful in the practice of this invention are commercially available from a number of manufacturers, including Dow Chemical (Midland, Mich.), Stockhausen (Greensboro, N.C.), and Chemdal (Arlington Heights, Ill.). One conventional granular superabsorbent polymer is based on poly(acrylic acid) which has been crosslinked during polymerization with any of a number of multi-functional co-monomer crosslinking agents, as is well known in the art. Examples of multifunctional crosslinking agents are set forth in U.S. Pat. Nos. 2,929,154; 3,224,986; 3,332,909; and 4,076,673. Other water-soluble polyelectrolyte polymers are known to be useful for the preparation of superabsorbents by crosslinking, these polymers include carboxymethyl starch, carboxymethyl cellulose, chitosan salts, gelatin salts, etc. They are not, however, commonly used on a commercial scale to enhance absorbency of disposable absorbent articles, primarily due to lower absorbent efficiency or higher cost.

Examples of binders useful in the absorbent structure of the present invention include polymeric binders in a solid or liquid form. The term "polymeric binder" refers to any compound capable of creating interfiber bonds between matrix fibers to increase the integrity of the ply. At the same time, the binder may optionally bind fibers and SAP particles to each other. For example, a dispersion of natural or synthetic elastomeric latex may be used as a binder. Examples of suitable latex binders are polymers and copolymers of acrylate, vinyl acetate and styrene-butadiene. Thermoplastic fibers or powder, which are well known in the art, are also commonly used to provide bonding upon heating of the absorbent structure to the melting point of the thermoplastic fiber or powder. Other binders, which can be used for stabilizing the absorbent structure of the present invention, include bonding agents used to bond cellulose fibers. These agents include polymers dispersed in water, which are cured after application to the fibrous web and create bonds between fibers or between fibers and SAP particles. Examples of such agents include various cationic starch derivatives and synthetic cationic polymers containing crosslinkable functional groups such as polyamide-polyamine epichlorohydrin adducts, cationic starch, dialdehyde starch and the like. Any combination of the above-described polymeric binders may be used for stabilizing the structure of the present invention. In one embodiment, the binder in the invention is a binding fiber, which comprises less than about 10% by weight of the SAP particles. In another example of the invention, the binder fibers comprise less than about 7% by weight of the absorbent structure.

As used herein, "integrity" is a measure of the tensile strength of a fibrous sheet, normalized for unit basis weight and is expressed in units (milliNewtons, Mn) of x-directional force required to break a 1 inch wide sample of the sheet per normalized basis weight of 1 gsm. In order to measure Wet Integrity (wet tensile strength) of an absorbent core or a commercial absorbent product, the following procedure is used:

1. 1 inch×4 inch samples are prepared. For samples with an obvious machine direction and cross direction, the 4-inch dimension is cut in the machine direction.
2. Remove any removable plastic backsheet, coverstock or synthetic acquisition material, leaving only the core.
3. Weigh sample. Apply 0.9% saline solution, in an amount equal to twice the sample weight, to the center of the sample using pipette or spray bottle (Example: sample weighs 1.00 g. Apply 2.00 g saline solution for total of 3.00 g).
4. Insert sample into Tensile Tester (for example a Thwing-Albert LT-150 Universal Materials Tester, default software settings used for test) by placing in pressurized clamps.
5. Start test.
6. When test is finished, record results displayed. These results include Force at Peak, Elongation at Peak, Maximum Elongation, Energy at Peak, and Energy at Maximum.

The Wet Integrity as used herein is defined as the Force at Peak as measured by using the above procedure. The Wet Integrity of the absorbent structures of the present invention are higher than 4.0 mN/gsm, and preferably higher than 6.0 mN/gsm.

Figure 3A:
FIG. 3 depicts a schematic representation of the apparatus for measuring softness.
Figure 3B:
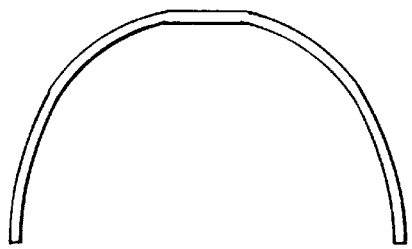
Figure 3C:
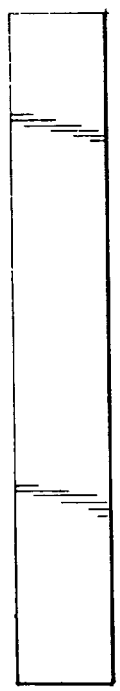

The softness of the absorbent structure is an important factor contributing to the overall conformability of the structure. As used herein, "softness" is the inverse of the amount of energy necessary to compress a sheet, in this case the sheet being the absorbent structure. The greater the amount of energy necessary to compress a sheet, the less soft it is. To measure softness of the core, the following procedure (a modified compression test) is used:

1. Prepare samples by cutting three 4 inch×8 inch pieces (if sample is a diaper, cut from the thicker section of diaper (if thickness is not uniform). For samples with obvious machine direction and cross direction, cut 8-inch dimension in machine direction.
2. Allow plastic backsheet and coverstock material to remain on sample (applies to commercial diaper samples). If testing prototype core samples, apply plastic backsheet, Exxon EMB-685 polyethylene film, to bottom of sample and coverstock, 15 gsm Avgol spunbond polypropylene, to top of sample (same size as sample, adhered with a small amount of spray adhesive).
3. Program modified compression test (for example, a Thwing-Albert LT-150 Universal Materials Tester): Compression test using following non-default settings: Break Detection Method=% Drop/Displacement, Break Value=% Drop=50, Distance Traps=0.3 in./0.5 in./0.7 in., Units: Distance/Displacement=inches; Force=grams, Test speed=1 in./min. All other settings left at defaults.
4. Insert sample into Tensile Tester using custom clamps as depicted in FIG. 3. Sample is inserted on its edge, such that it will be compressed in the y-direction (4-inch direction), having 1 inch on both edges within the custom clamps, thus leaving a 2-inch gap.
5. Start test.
6. When deflection exceeds 0.7 inch, push down on top pressurized clamp to simulate a sample break and stop the test (does not affect test results). Record results displayed. These results include Force at Peak, Deflection at Peak, Maximum Deflection, Energy at Peak, and Energy at Maximum Deflection, and Force at Distance Traps.

The value, which is used to calculate the softness, is Energy at Maximum Deflection, which is expressed in Joules. Energy of Maximum Deflection, $E_{d\,max}$, is calculated according to the following formula:

$$E_{d\,max_{d\,max}} = \int^{d\,max} F\,d_d$$

where $E_{d\,max}$ is Energy at Maximum Deflection, F is force at given deflection, d, and d min and d max are the deflections at the start of the test and at the end of the test, respectively.

Softness, S, is defined here according to the following formula:

$$S = 1/(\text{Energy at Maximum Deflection}).$$

The result, S, is expressed here in 1 per Joule, 1/J.

In general, Softness of the overall absorbent structure of the present invention should be higher than 8.0/J, preferably higher than 15/J.

The pliability of the absorbent structure is also an important factor contributing to the overall conformability of the sheet. As used herein, "pliability" is the inverse of the amount of force necessary to bend a sheet, in this case the sheet being the absorbent structure of the invention. The greater the force necessary to bend the sheet, the less pliable the sheet is.

Pliability can be measured by the following procedure, using a Gurley tester (Model 4171, Gurley Precision Instruments, Trey, N.Y.).

Figure 2:
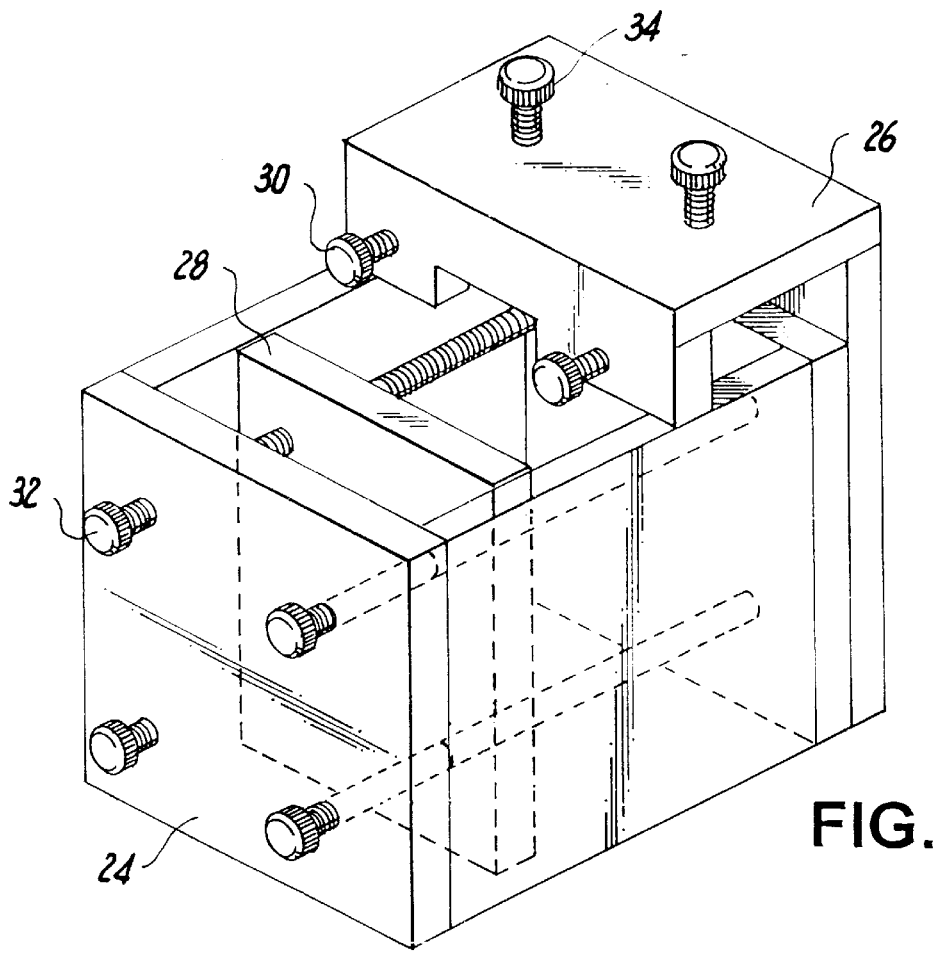
FIG. 2 is a schematic representation of a modified clamp used in a Gurley tester.

1. Cut sample to 1 inch×3.25 inch as accurately as possible. If there is a definite machine direction and cross direction, cut one sample in each direction and test each.
2. Fit custom clamp as shown in FIG. 3, over the original clamp provided with the Gurley tester, and tighten smaller, upper thumbscrews to secure (see FIG. 2 illustrating the custom clamp for higher basis weight, lofty sheets). The custom clamp was designed in such a way that it does not change the thickness of the tested material, where the material is inserted into the clamp. If the thickness is changed as a result of clamping then the properties of the structure are changed and the results obtained by using the Gurley tester are affected. In the present method, the clamp of FIG. 3 is used to eliminate such undesired effects.
3. Open the custom clamp adjustable plate by loosening longer, lower thumbscrews. Place sample in clamp by sliding sample up until it just contacts original clamp. There should be 2.0 inches of sample contained in the custom clamp.
4. Adjust height of custom clamp by loosening height adjustment screw on original clamp. Adjust height so that a gap of 1.0 inch exists between the point where the sample exits the custom clamp and the point where the sample will contact the lever arm.
5. Ensure that the remaining 0.25 inch of sample extends below the top of the lever arm. Ensure that lever arm is not moving. Press motor button to move sample towards lever arm. Continue pressing motor button until sample clears lever arm. While doing this, observe and note the highest number reached on the scale. Repeat this in the opposite direction.
6. Average the two values obtained. In the conversion chart on the apparatus, find the factor for a 1 inch wide×1.5 inch long sample depending on the weight used and the distance the weight was placed from the center on the lever arm. A 1.0 inch×3.25 inch sample tested using the custom clamp corresponds to a 1.0 inch×1.5 inch sample tested without using the custom clamp. Without the custom clamp, 0.25 inch of sample is in the original clamp, 0.25 inch extends below the top of the lever arm, and 1 inch is the gap between. Using the custom clamp, the same 0.25-inch number in the custom clamp is used; the other 1.75-inch in the custom clamp secures the thicker sample in place. The same 0.25-inch extends below the top of the lever arm and the same one-inch gap is in between.
7. Multiply the average reading on the scale by the appropriate conversion factor found on the chart.

The result is Stiffness, which is expressed in milligrams force, mg. Pliability, P, is defined here according to the following formula:

$$P = 10^6/9.81 * \text{Stiffness}.$$

The result, P, is expressed here in 1 per Newton, 1/N. In general, Pliability of the entire absorbent structure of the present invention is higher than 60/N, preferably higher than 80/N.

In the present invention, high levels of softness, pliability and wet integrity have been achieved by applying one or a combination of the following features in the preparation of an absorbent structure: by using soft fibers, curled or crimped fibers, by applying soft binder systems, such as for example fine or crimped binding fibers, elastic latex binders or water-soluble bonding agents, by minimizing the amounts of binder, applying relatively low pressure during compaction before curing, and using relatively low pressure during the calandering of the sheet after it has been cured. In general, the density of the sheet after compaction and/or calandering in the absorbent structures of the invention should be lower than 0.35 g/cc, and preferably lower than 0.3 g/cc.

In one embodiment of the invention, no carrier tissue sheet is used in the web forming process. Such carrier tissue sheets are usually used and become an integral part of the structure. They increase the strength of the web but increase its stiffness.

In another embodiment of the invention, the amount of binding fiber in the structure is less than 10% by weight of the structure. In another embodiment the amount of binding fiber is lower than 7% by weight of the structure. Typically, higher amounts of binders are used which result in an absorbent structure of relatively high integrity but low pliability.

In another embodiment of the invention the softness and pliability of the structure is achieved by mechanical treatment of the entire structure or of its component absorbent plies after formation of the absorbent plies. Such mechanical treatments include microcreping, passing the web through the nip between grooved rolls and the like. In general, in these procedures some of the bonds within the structure are disrupted and, as a result, the structure becomes more conformable.

The integrity of the absorbent structure of this invention is higher than that of a conventional core made with only fluff and SAP powder and is sufficiently high to allow the sheet of the core to be used in conversion. In particular, the wet integrity of the absorbent structure of this invention is higher than that of conventional cores and of airlaid cores made without binders. In one embodiment, the absorbent core has a wet integrity greater than 4.0 mN/gsm. In another embodiment, the absorbent core has a wet integrity greater than 6.0 mN/gsm. In yet another embodiment, the absorbent core has a wet integrity greater than 8.0 mN/gsm. The wet integrity of conventional cores and airlaid cores made without any binders is relatively low and is commonly below 4.0 mN/gsm (see Table 1). In the conventional cores (formed in place), integrity is mainly dependent on mechanical entanglement of fluff fibers. Since such a mechanical entanglement is due to in part to the amount of curl of the fibers, and this curl is lost at least to some extent when the material is wetted. The integrity of the conventional core is also decreased substantially in the wet state. In the case of airlaid materials (such as described in U.S. Pat. Nos. 5,866,242 or 5,916,670), which are made without any binders but are highly densified, the densified structures are held together mainly with the aid of hydrogen bonds. However, such bonds are broken completely when the material is wetted and then the absorbent core becomes very weak.

The softness and pliability of the absorbent structure of the present invention are high enough that the material may conform easily to the shape of the human body or to the shape of a component (for example another absorbent layer) of the absorbent article adjacent to it. In one embodiment, the softness of the absorbent structure is higher than 8.0/J and the pliability of the absorbent structure is higher than 60/N.

To further increase the levels of softness, pliability and wet integrity of the absorbent structure, the structure may be treated using various chemical and/or mechanical processes. Without being bound by any theory, it is believed that, for a given composition of the absorbent structure, the desired level of softness, pliability, and wet integrity can be achieved with an appropriate ratio of bonded to unbonded structural elements. If the number of bonds between the fibers or between the fibers and SAP particles is too small, then the wet integrity of the structure is too low to achieve improved performance of the absorbent structure during use. When the user moves then such a low-integrity structure may not withstand mechanical stresses and may produce cracks and other discontinuities, leading to poor liquid containment and subsequent leaks. On the other hand, if the number of bonds in the absorbent structure is too high, then pliability and softness are too low and the structure becomes less conformable, degrading performance due to formation of undesirable channels and gaps through which the liquid may freely flow and leak out of the absorbent article.

As exemplified below, the absorbent structure may be used in combination with a carrier such as cellulose tissue or a synthetic nonwoven. The absorbent structure may also be used in combination with other layers or structures to form an absorbent structure.

In another preferred embodiment, the upper ply of the structure is used separately as an absorbent structure. The one ply structure exhibits high wet integrity, high softness and high pliability, and can be used in a variety of applications requiring such attributes. Examples of such applications include disposable absorbent articles such as disposable diapers, sanitary pads, adult incontinence products and training pants.

The one ply absorbent structure can be made as set forth in the examples relating to the two-ply structures. Alternatively, the one ply structure may be made using an airlaid machine employing three forming heads. Examples using such a machine are set forth below as Examples 8 to 11.

The invention is further described in the following non-limiting examples.

In the following examples basis weights (in gsm) are set forth as targets. Actual basis weights obtained may vary by up to ±10%.

EXAMPLE 1

An absorbent structure was assembled by joining together upper ply (component A1) and lower ply (component B 1) described below. Both absorbent components were made by dry forming (or airlaying) on an M&J pilot machine. The mechanical and absorbency properties of the structure are depicted in Tables 1, 3 and 4. The structure exhibited improved performance compared to the performance found with commercial structures as described herein, due to the combination of profiled absorbency and appropriate levels of conformability and integrity.

Component A1. Two forming heads were used and they were fed with the same composition and amount of raw materials. The product was laid on a carrier of 40 gsm Brand 6810 polyester (polyethylene terephthalate) nonwoven (PGI). This material constituted the top stratum of the upper ply. The basis weights and compositions of the middle stratum and of the bottom stratum were the same, the basis weight being 160 gsm and the composition being 56.3% HPF fluff (Buckeye Technologies Inc., Memphis, Tenn.), 37.5% Z1049 SAP (Stockhausen, Greensboro, N.C.) and 6.2% T-255, 2.8 dpf (denier per fiber) thermoplastic, bicomponent binder fiber (Kosa, Salisbury, N.C.). The sheet was calandered after curing (160° C.; 1 min. dwell) with minimum pressure to a thickness of 3 mm.

Component B 1. The first forming head was fed with Foley Fluff (Buckeye Technologies) at 75 gsm and T-255 binder fiber (Kosa, Salisbury, N.C.) at 3 gsm. The formed layer was the middle stratum of the Lower Ply. The top stratum of the lower ply was formed by the second forming head, which was fed with Foley Fluff (Buckeye Technologies) at 55 gsm, T-255 binder fiber (Kosa, Salisbury, N.C.) at 12 gsm, and SXM4750 SAP (Stockhausen, Greensboro, N.C.) at 215 gsm. The product was laid on a carrier, which was Duni Finner K1801 cellulose tissue (Duni, Kisa, Sweden). The carrier constituted the bottom stratum of the lower ply. The sheet was calandered after curing to a thickness of 2 mm.

The components were assembled by placing a 10×20 cm A1 sheet of material over one end of a 10×40 cm B1 sheet of material. Measurements were made at the end where the A1 and B 1 sections overlapped.

EXAMPLE 2

An absorbent structure was assembled by joining together Components A2 and B2 described below. Both absorbent components were made by dry forming on an M&J pilot machine. In the resultant structure component A2 is the upper ply and component B2 is the lower ply. The mechanical and absorbency properties of the structure are depicted in Tables 1, 3 and 4. The structure exhibited improved performance due to the combination of profiled absorbency and appropriate levels of conformability and integrity.

Component A2. The middle stratum of the Upper Ply was formed by feeding the first forming head with HPF fluff (Buckeye Technologies, Memphis, Tenn.) at 40 gsm and 2.8 dpf T-255 binder fiber (Kosa, Salisbury, N.C.) at 2.5 gsm. The second head was used to form the top stratum of the upper ply. The second forming head was fed with HPF fluff (Buckeye Technologies, Memphis, Tenn.) at 100 gsm, Z1049 SAP (Stockhausen, Greensboro, N.C.) at 94 gsm, and 2.8 dpf T-255 binder fiber (Kosa, Salisbury, N.C.) at 13 gsm. The product was laid on a carrier, which was 48 gsm Licontrol™ 381002 (polypropylene) nonwoven (Jacob-Holm Industries, Soultz, France). This carrier constituted the top stratum of the upper ply. The product was calandered after curing with minimum pressure to a thickness of 3.0 mm.

Component B2. Two forming heads were used and they were fed with the same composition and amount of raw materials. The product was laid on a carrier, which was Duni Finner K1801 cellulose tissue. The composition of the overall component B2 having a basis weight of 378 gsm was 34.1% Foley Fluff (Buckeye Technologies), 57.1% SXM3950 SAP (Stockhausen, Greensboro, N.C.), and 4% T-255, 2.8 dpf binder fiber (Kosa, Salisbury, N.C.); the balance of the structure was a carrier tissue of 18 gsm. The sheet was calandered after curing to a thickness of 2 mm.

EXAMPLE 3

An absorbent structure was assembled by joining together Components A3 and B3 described below. Both absorbent components were made by dry forming on a DanWeb pilot machine. In the resultant structure Component A3 is the upper ply and Component B3 is the lower ply. The mechanical and absorbency properties of the structure are depicted in Tables 1, 3 and 4. The structure exhibited improved performance due to the combination of profiled absorbency and appropriate levels of conformability and integrity.

Component A3. The first forming head was fed with Foley Fluff (Buckeye Technologies, Memphis, Tenn.) at 60 gsm and 2.8 dpf T-255 binder fiber (Kosa, Salisbury, N.C.) at 10 gsm, to form the bottom stratum of the upper ply. The second head was used to form the middle stratum of the upper ply. The second head was fed with Foley Fluff at 98 gsm, SXM70 SAP (Stockhausen, Greensboro, N.C.) at 62.5 gsm, and 2.8 dpf T-255 binder fiber (Kosa, Salisbury, N.C.) at 19.5 gsm. The third head was fed with Wellman 376×2 polyester fibers having thickness of 15 dpf and length of 6 mm at 35 gsm. The top stratum of the upper ply thus formed was sprayed with A-181 latex (Air Products, Allentown, Pa.) diluted to 10% solids at 5 gsm. The sheet was calandered after curing with minimum pressure to a thickness of 4.1 mm.

Component B3. One forming head was used and it was fed with ND416 fluff(Weyerhaeuser, Tacoma, Wash.) at 128 gsm, SXM70 SAP (Stockhausen, Greensboro, N.C.) at 225 gsm and 2.8 dpf T-255 binder fiber (Kosa, Salisbury, N.C.) at 22 gsm. The product was laid on a Cellutissue 3024 cellulose tissue carrier. The sheet was calandered after curing to a thickness of 1.9 mm.

EXAMPLE 4

An absorbent structure was assembled by joining together Components A4 and B4 described below. Both absorbent components were made by dry forming on a DanWeb pilot machine. In the resultant structure Component A4 is the upper ply and Component B4 is the lower ply. The mechanical and absorbency properties of the structure are depicted in Tables 1, 3 and 4. The structure exhibited improved performance due to the combination of profiled absorbency and appropriate levels of conformability and integrity.

Component A4. The first forming head was fed with Foley Fluff (Buckeye Technologies, Memphis, Tenn.) at 77.6 gsm and 2.8 dpf T-255 binder fiber (Kosa, Salisbury, N.C.) at 12.4 gsm, forming the bottom stratum of the upper ply. The second head was used to form the middle stratum of the upper ply. The second head was fed with Foley Fluff at 102 gsm, SP 1186 SAP (Stockhausen, Greensboro, N.C.) at 130 gsm, and 2.8 dpf T-255 binder fiber (Kosa, Salisbury, N.C.) at 28 gsm. The third head was fed with Wellman 376×2 polyester fibers having thickness of 15 dpf and length of 6 mm, at 42 gsm. The top stratum of the Upper Ply thus formed was sprayed with A-124 latex (Air Products, Allentown, Pa.) diluted to 10% solids at 8 gsm. The sheet was calandered after curing with minimum pressure to a thickness of 5.7 mm.

Component B4. The first and second forming heads were fed with equal amounts of all components, that is with ND416 fluff (Weyerhaeuser, Tacoma, Wash.) at 37 gsm, SXM3950 SAP (Stockhausen, Greensboro, N.C.) at 92.3 gsm and 2.8 dpf T-255 binder fiber (Kosa, Salisbury, N.C.) at 5 gsm. The web thus formed became the bottom stratum of the lower ply. This stratum was laid on a Cellutissue 3024 cellulose tissue carrier. The third head was fed with ND416 fluff at 38.5 gsm and 2.8 dpf T-255 binder fiber at 8.9 gsm, forming the top stratum of the lower ply. The final sheet was calandered after curing to a thickness of 1.45 mm.

EXAMPLE 5

The structures of Examples 1, 2, 3 and 4 were analyzed for Wet Integrity, Softness and Pliability. The results obtained are summarized in Table 1. In Table 1 are summarized also the results of the analysis of the absorbent cores of several commercial disposable infant diapers (samples A, B and C) and a sample of a high-density airlaid material made with fluff and SAP and without any binder (sample D). Determination of basic structural parameters of the tested cores are shown in Table 2. The data in Table 1 demonstrate that the absorbent structures of Examples 1, 2, 3 and 4 have much higher Wet Integrity than all the other tested commercial cores and much higher softness and pliability than the core of sample D.

TABLE 1

| Absorbent Structure | Wet Integrity mN/gsm | Softness, 1/J | Pliability, 1/N |
|---|---|---|---|
| Example 1 | 5.2 | 8.9 | 72.9 |
| Example 2 | 7.2 | 10.2 | 112.0 |
| Example 3 | 8.7 | 17.8 | 104.0 |
| Example 4 | 7.0 | 10.6 | 105.2 |
| Example A | 0.8 | 10.1 | 175.5 |
| Example B | 2.6 | 12.9 | 137.8 |
| Example C | 1.5 | 7.4 | 117.7 |
| Example D | 1.3 | 5.6 | 40.2 |

TABLE 2

| Sample | Upper core width × length (cm × cm) | Lower core width × length (cm × cm) | Assembled surface area (cm$^2$) | Upper core Basis Weight (gsm) | Lower core Basis Weight (gsm) | Overall average Basis Weight (gsm) | Upper core Density (g/cc) | Lower core Density (g/cc) | Overall average core Density (g/cc) | Upper core % SAP | Lower core % SAP | Overall average core % SAP |
|---|---|---|---|---|---|---|---|---|---|---|---|---|
| Example D | 8 × 20 | 11 × 36 | 396 | 400 | 310 | 472 | 0.27 | 0.36 | 0.31 | 37.0 | 51.0 | 43.0 |
| Example C | | | 385 | | | 759 | | | 0.14 | | | 26.7 |
| Example B | | | 468 | | | 617 | | | 0.25 | | | 53.5 |
| Example A | | | 360 | | | 649 | | | 0.26 | | | 43.4 |
| Example 1 | 10 × 20 | 10 × 40 | 400 | 360 | 375 | 555 | 0.12 | 0.19 | 0.16 | 37.5 | 57.3 | 47.6 |
| Example 2 | 10 × 20 | 10 × 40 | 400 | 297.5 | 360 | 509 | 0.10 | 0.18 | 0.14 | 26.1 | 60.0 | 44.7 |
| Example 3 | 9 × 20 | 10 × 40 | 400 | 290 | 390 | 521 | 0.07 | 0.21 | 0.15 | 21.6 | 57.7 | 42.3 |
| Example 4 | 10 × 20 | 10 × 40 | 400 | 400 | 331 | 531 | 0.07 | 0.23 | 0.14 | 32.5 | 55.8 | 43.1 |

EXAMPLE 6

The structures made according to the procedures described in Examples 1, 2, 3, and 4 were tested for liquid acquisition properties. To evaluate the acquisition properties, the Acquisition Time was measured, that is the time, for a given volume of saline solution to be absorbed by an absorbent structure (until any free liquid disappears from the surface of the absorbent).

The following method was used to measure the Acquisition Time:

1. Condition sample in lab at 70° F. and 50% relative humidity for 2 hours prior to testing.
2. Prepare standard saline solution (0.9% NaCl/DI H$_2$0 by weight). Add dye if desired.
3. Determine insult volume and load to be used. Medium capacity samples (most diapers of medium size (size #3)) use 3×75 ml insults and 0.4-psi load. The absorbent structures described in Examples 1–4 belong to this category.
4. If sample is formed in lab or on pilot machine (airlaid), cut to required dimensions. This is 4 inches×14 inches for samples made on the lab pad former, 4 inch×16 inches for samples made on the pilot machine. If sample is a commercial diaper, simply cut elastic legbands so that diaper will lay flat. Take weight/thickness measurements of each sample.
5. Prepare airlaid samples by placing on plastic backsheet, Exxon EMB-685 polyethylene film, and adding coverstock material, 15 gsm Avgol spunbond polypropylene. Ensure that plastic backsheet material edges fold up toward top of sample to protect against leakage while testing.
6. Place sample in acquisition apparatus by placing sample on bottom plate, positioning foam piece on top of sample, placing insult ring into hole in foam, and then positioning weighted top plates over foam piece.
7. Set timer for 20 minutes and place beside test apparatus.
8. With stopwatch in one hand and graduate cylinder containing insult volume in other hand, prepare to insult sample. Pour fluid into insult ring. Start stopwatch at moment the fluid strikes the sample. Empty fluid from cylinder as quickly as possible. Stop stopwatch when fluid is absorbed by sample.
9. Note time taken by sample to absorb fluid. Start 20 minute timer as soon as fluid is absorbed by sample.
10. After 20 minutes, repeat steps 7–9.
11. After another 20 minutes, repeat steps 7–9. Note: If no other tests are to be done after the Acquisition test, the 20-minute interval following the third insult can be omitted. However, if another test is to be done following the Acquisition test (Rewet and Retention or Distribution), the 20-minute interval must be used and then the other test may be started.

The following formula is used to calculate the Acquisition Rate:

$$\text{Acquisition Rate (ml/s)} = \frac{\text{Insult Volume (ml)}}{\text{Aquisition Time (s)}}$$

The results obtained from testing the structures of Examples 1, 2, 3, and 4 are collected in Table 3. In Table 3 are summarized also the results of the analysis of the absorbent cores of some commercial diaper articles samples A, B and C and of another commercial diaper core, sample D, and having basic physical properties as described in Table 2. The data in Table 3 includes the results obtained from testing the structures of Examples 1, 2, 3, and 4. The structures of these Examples were assembled according to the illustration in FIG. 1. The length of the Upper Plies in these structures was 20 cm in each case. The results in Table 3 indicate that absorbent structures of Examples 1, 2, 3, and 4 have considerably shorter Acquisition Times than sample D. It can also be seen that the absorbent structures of Examples 3 and 4 have shorter Acquisition Times than those of the cores of all the tested commercial diapers.

TABLE 3

| Absorbent Structure | 1st Acquisition Rate, ml/s | 2nd Acquisition Rate, ml/s | 3rd Acquisition Rate, ml/s |
|---|---|---|---|
| Example 1 | 1.16 | 0.56 | 0.36 |
| Fxample 2 | 1.35 | 0.86 | 0.63 |
| Example 3 | 2.85 | 1.29 | 0.93 |
| Example 4 | 5.56 | 2.71 | 1.83 |
| Example A | 2.01 | 1.19 | 0.83 |
| Example E | 2.25 | 1.70 | 1.24 |
| Example B | 1.90 | 0.75 | 0.55 |
| Example C | 1.32 | 0.46 | 0.33 |
| Example D | 0.91 | 0.49 | 0.30 |

EXAMPLE 7

The structures made according to the procedures described in Examples 1, 2, 3 and 4 were tested for rewet. In order to evaluate the rewet, the Rewet was measured, that is the amount of liquid, which can be detected on the surface of the absorbent structure after its saturation with a given amount of saline.

The following method was used to measure Rewet:

The Rewet and Retention Test is designed to be performed immediately following the Acquisition Test. The Acquisition Test procedure must be followed before starting this test. If no acquisition information is needed, acquisition times do not have to be recorded, however the pattern of 3 insults separated by 20-minute intervals must be followed. It is imperative that the 20 minute interval has elapsed before starting this test. Sample/solution preparation is the same as in the Acquisition test (See Acquisition Test document).

1. Sample is now assumed to have been through the Acquisition Test and left undisturbed for the final 20-minute time interval. Set a timer for 5 minutes and place beside test apparatus.
2. Weigh stack of 10 Buckeye S-22 Blotter papers cut to same dimension as sample.
3. Remove weight over sample, foam piece, and insult ring.
4. Place stack of papers on sample.
5. Replace foam piece and weights over sample. Start 5-minute timer.
6. At end of 5 minutes, remove weight and weigh stack of papers.

Note weight differences between wet and dries papers. The rewet is calculated according to the formula:

Rewet (g)=Weight of wet papers (g)−weight of dry papers (g)

The following formula is used to calculate the Rewet Retention after the third insult:

$$\text{Rewet Retention (\%)} = \frac{(\text{Rewet (g)} \times 1 \text{ ml/g}) \times 100}{\text{Vol. of All Insults (ml)} - \text{Volume of ALL insults (ml)}}$$

The structures of Examples 1, 2, 3, and 4 were tested for Rewet and the results are presented in Table 4. The data in Table 3 includes the results obtained from testing the structures of Examples 1,2,3 and 4. The structures of these Examples were assembled according to the illustration in FIG. 4. The length of the Upper Plies in these structures was 20 cm in each case. In Table 4 are summarized also the results of the analysis of the absorbent cores of some commercial diaper articles, samples A, B and C and of the commercial core, sample D, as described in Table 2. The data in Table 4 indicate that except for the Sample of Example E, had the lowest Rewet Retention value, all the other tested cores had Rewet Retention values at least 97%.

TABLE 4

| Absorbent Structure | Rewet Retention, % |
|---|---|
| Example 1 | 97.0 |
| Example 2 | 98.4 |
| Example 3 | 99.4 |
| Example 4 | 97.2 |
| Example A | 98.5 |
| Example E | 92.8 |
| Example B | 99.8 |
| Example C | 99.0 |
| Example D | 97.1 |

EXAMPLE 8

An absorbent structure was made by dry-forming on a DanWeb pilot machine. The mechanical and absorbency properties of the structure are depicted in Tables 5 and 6. The structure exhibited improved performance due to the combination of appropriate levels of softness, pliability and wet integrity. Three forming heads were used to make the absorbent structure. The product was laid on a carrier of Cellutissue 3024 having basis weight of 18 gsm. Prior to use, this tissue was impregnated with 4 gsm bicomponent binder fiber, T-255 (Kosa Salisbury, N.C.), having thickness of 2.8 denier per fiber. This fiber was deposited on the carrier tissue on the DanWeb pilot machine and cured to bond the bicomponent fiber to the tissue. The purpose of this was to obtain a good adhesion of the carrier to the product formed on it. The carrier tissue constituted the bottom stratum of the absorbent structure. To construct the lower middle stratum, the first forming head of the machine was fed with 96 gsm ND416 fluff (Weyerhaeuser, Tacoma, Wash.) and 115 gsm superabsorbent polymer SXM70 (Stockhausen, Greensboro, N.C.). Then, during the process, the upper middle stratum was formed by feeding the second forming head with 62 gsm of Foley Fluff (Buckeye Technologies, Memphis, Tenn.), 25 gsm of superabsorbent polymer SXM70, and 12 gsm of bicomponent binder fiber, T-255. Finally, the top stratum was formed by feeding the third forming head with 42 gsm Wellman 376X2 polyester fiber, of which the thickness was 15 denier per fiber and the length was 6 mm. The top stratum was sprayed with 6 gsm of latex A-181 (Air Products, Allentown, Pa.), at a concentration of 10% solids. The sheet was compacted to the thickness of 2.6 mm and cured.

EXAMPLE 9

An absorbent structure was made by dry-forming on a DanWeb pilot machine. The mechanical and absorbency properties of the structure are depicted in Tables 5 and 6. The structure exhibited improved performance due to the combination of appropriate levels of softness, pliability and wet integrity. Three forming heads were used to make the absorbent structure. The bottom stratum was formed by feeding the first forming head with 83 gsm Foley Fluff and 7 gsm bicomponent binder fiber T-255, having thickness of 2.1 denier per fiber. The middle stratum was formed by feeding the second forming head with 110 gsm Foley Fluff, 130 gsm superabsorbent polymer SP 1186 (Stockhausen, Greensboro, N.C.) and 15 gsm bicomponent binder fiber T-255, having thickness of 2.1 denier per fiber. The top stratum was formed by feeding the third forming head with 42 gsm Wellman 376X2 polyester fiber, of which the thickness was 15 denier per fiber and the length was 6 mm. The top stratum was sprayed with 8 gsm latex A-181, at a concentration of 10% solids. The sheet was compacted to the thickness of 5.2 mm and cured.

EXAMPLE 10

An absorbent structure was made by dry-forming on a DanWeb pilot machine. The mechanical and absorbency properties of the structure are depicted in Tables 5 and 6. The structure exhibited improved performance due to the combination of appropriate levels of softness, pliability and wet integrity. The product was laid on a carrier, which was Cellutissue 3024 having basis weight of 18 gsm. Prior to use this tissue was impregnated with 4 gsm of bicomponent binder fiber, T-255, having thickness of 2.8 denier per fiber. The carrier tissue constituted the bottom stratum of the absorbent structure. In order to construct the lower middle stratum, the first forming head was fed with ND416 fluff (Weyerhaeuser, Tacoma, Wash.) at 80 gsm, and superabsorbent polymer SXM70 at 100 gsm. The upper middle stratum was formed with the second forming head by feeding it with Foley fluff at 79 gsm and superabsorbent polymer SXM70 at 38 gsm. The top stratum was formed with the third forming head with Wellman 376X2 poly(ethylene terephtalate) having the thickness of 15 denier per fiber and the length of 6 mm. This fiber was fed at 38 gsm. The product was sprayed from the top with an aqueous solution of Kymene 557H wet strength resin (Hercules, Willmington, Del.) at 10% solids. The target basis weight of Kymene solids on the web was 7 gsm. Due to the pressure gradient resulting from the difference between the higher pressure at the top stratum of the formed structure and the lower pressure under the forming wire the solution of the bonding agent could penetrate to some extent to the strata below, so the Kymene could bond both the top stratum and the strata below. The product was calandered to get the thickness of 2.6 mm.

EXAMPLE 11

An absorbent core was made by dry-forming on an M&J commercial machine with three forming heads. The product was laid on a carrier, which was Cellutissue 3024 having basis weight of 18 gsm. The bottom stratum was formed by feeding the first and the second heads with equal amounts of ND416 fluff, superabsorbent polymer SXM3950 (Stockhausen, Greensboro, N.C.) and bicomponent binder fiber T-255 having a thickness of 2.8 denier per fiber. The composition of the bottom stratum thus formed, by total weight of this stratum, was 23.2% ND416, 48.2% SXM3950 and 2.6% T-255. The middle stratum was formed by feeding the third head with ND416 at 38.1 gsm and T-255 at 9 gsm. The product thus formed was joined with Licontrol 381002-48, a 48 gsm synthetic nonwoven (Jacob Holm Industries, Soultz, France), which constituted the top stratum of the structure. The structure was analyzed for mechanical and absorbency properties. The results are depicted in Tables 5 and 6. The structure exhibited improved performance due to the combination of appropriate levels of softness, pliability and wet integrity.

The structures of Examples 8–11 were analyzed for Wet Integrity, Softness and Pliability. The obtained results are summarized in Table 6. In Table 6 are also given the results of the tests carried out with a number of commercial diaper cores. The data in Table 6 indicate that absorbent structures of Examples 8–11 have higher Wet Integrity, higher Softness and higher Pliability than all the other tested absorbent cores.

TABLE 6

| Absorbent Structure | Wet Integrity mN/gsm | Softness, 1/J | Pliability, 1/N |
|---|---|---|---|
| Example 8 | 6.5 | 30.4 | 272.7 |
| Example 9 | 12.3 | 37.5 | 235.5 |
| Example 10 | 8.1 | 22.1 | 259.9 |
| Example 11 | 6.5 | 13.1 | 199.6 |
| Example A | 0.8 | 10.1 | 175.5 |
| Example E | 4.2 | 12.4 | 196.7 |
| Example B | 2.6 | 12.9 | 137.8 |
| Example C | 1.5 | 7.4 | 47.7 |
| Example D | 1.3 | 5.6 | 40.2 |

EXAMPLE 13

The structures made according to the procedures described in Examples 8–11 were tested for rewet according to the method described above in Example 7. as described. The results of the Rewet retention for the structures of Examples 8–11 and an commercial absorbent core (Example E) are set forth in Table 7. It can be seen that the Rewet Retention values of the structures of Examples 8–11 are as good or better than the Rewet Retention value for the commercial structure (Example E).

TABLE 7

| Absorbent Structure | Rewet Retention, % |
|---|---|
| Example 1 | 97.3 |
| Example 2 | 83.3 |
| Example 3 | 98.3 |
| Example 4 | 99.1 |
| Example E | 84.6 |

TABLE 5

| Sample | Overall surface area (cm2) | Overall average Basis Weight (gsm) | Overall average core Density (g/cc) | Overall average core % SAP |
|---|---|---|---|---|
| Example D | 398 | 472 | 0.31 | 43.0 |
| Example C | 385 | 759 | 0.14 | 26.7 |
| Example B | 468 | 617 | 0.25 | 53.5 |
| Example E | 260 | 547 | 0.11 | 44.9 |
| Example A | 360 | 649 | 0.26 | 43.4 |
| Example 8 | 320 | 380 | 0.15 | 36.8 |
| Example 9 | 320 | 395 | 0.08 | 32.9 |
| Example 10 | 320 | 364 | 0.14 | 37.9 |
| Example 11 | 320 | 387 | 0.21 | 58.1 |

What is claimed is:

1. An absorbent structure having wet integrity higher than about 4.0 mN/gsm, softness higher than 8.0/J, pliability higher than about 70/N, and providing a substantially dry liquid-accepting surface after receiving a quantity of liquid, said structure comprising:
   a) an upper ply having an upper fluid receiving surface and a lower surface and comprising:
      i) a top stratum comprising synthetic matrix fibers bonded with a binder, said matrix fibers having length from about 2 to about 15 mm;
      ii) a middle stratum in fluid communication with the top stratum, the middle stratum including natural fibers, superabsorbent particles and a binder; and iii) a bottom stratum in fluid communication with the middle stratum, the bottom stratum including natural fibers and a binder; and b) a lower ply in fluid communication with the upper ply, the lower ply having an upper surface and a lower surface and including at least one stratum including natural fibers, superabsorbent polymer particles, and a binder, wherein the lower surface of the upper ply has a surface area less than about 80% of the upper surface area of the lower ply;

c) the basis weight of the top stratum of the upper ply is from about 20 gsm to about 120 gsm;

d) the binder content (per cent by weight) in the top stratum of the upper ply is from about 5% to about 20%;

e) the basis weight of the middle stratum of the upper ply is from about 50 gsm to about 1000 gsm;

f) the binder content (per cent by weight) in the middle stratum of the upper ply is from about 1% to about 10%;

g) the basis weight of the bottom stratum of the upper ply is from about 10 gsm to about 150 gsm;

h) the binder content (per cent by weight) in the bottom stratum of the upper ply is from about 5% to about 15%;

i) the superabsorbent particle content (per cent by weight) in the upper ply is lower than the content of superabsorbent particles in the lower ply;

j) apparent density of the upper ply is lower than the apparent density of the lower ply;

k) the basis weight of the lower ply is from about 100 gsm to about 1000 gsm;

l) apparent density of the lower ply is about 0.15 g/cc to about 0.25 g/cc;

m) the binder content (per cent by weight) in the lower ply is from about 1% to about 8%; and n) the lower ply contains at least 30% superabsorbent particles of the basis weight of the lower ply.

2. An absorbent structure having wet integrity higher than about 4.0 mN/gsm, softness higher than 8.0/J, pliability higher than about 70/N, and providing a substantially dry liquid-accepting surface after receiving a quantity of liquid, said structure comprising:

a) an upper ply having an upper fluid receiving surface and a lower surface and comprising:
i) a top stratum comprising synthetic matrix fibers bonded with a binder, said matrix fibers having length from about 2 to about 15 mm;
ii) a middle stratum in fluid communication with the top stratum, the middle stratum including natural fibers, superabsorbent particles and a binder; and
iii) a bottom stratum in fluid communication with the middle stratum, the bottom stratum including natural fibers and a binder; and b) a lower ply in fluid communication with the upper ply, the lower ply having an upper surface and a lower surface and including at least one stratum including natural fibers, superabsorbent polymer particles, and a binder, wherein the lower surface of the upper ply has a surface area less than about 80% of the upper surface area of the lower ply.

3. The absorbent structure of claim 1 wherein the length of the synthetic matrix fibers is from about 4 to about 12 mm.

4. The absorbent structure of claim 1 wherein the synthetic matrix fibers are from about 2 to about 30 denier per fiber.

5. The absorbent structure of claim 4 wherein the synthetic matrix fibers are from about 6 to about 15 denier per fiber.

6. The absorbent structure of claim 1 wherein the synthetic matrix fibers are selected from the group consisting of polyethylene, polypropylene, polyester, polyamide, cellulose acetate, rayon fibers, and mixtures thereof.

7. The absorbent structure of claim 1 wherein the binder is selected from the group consisting of latex binders, thermoplastic powders, thermoplastic fibers, bicomponent fibers and mixtures thereof.

8. The absorbent structure of claim 1 wherein the binder is selected from the group consisting of polyamide-polyamine epichlorohydrin adducts, cationic starch, dialdehyde starch, poly(vinyl alcohol), chitosan and mixtures thereof.

9. The absorbent structure of claim 1 wherein said natural fibers are selected from the group consisting of cotton, softwood pulps, hardwood pulps, straw, keaf fibers, cellulose fibers modified by chemical, mechanical and/or thermal treatments, keratin fibers, and mixtures thereof.

10. The absorbent structure of claim 1 wherein the basis weight of the top stratum of the upper ply is from about 30 gsm to about 60 gsm.

11. The absorbent structure of claim 1 wherein the content of synthetic matrix fibers in the top stratum of the upper ply is from about 50 to about 99% by weight.

12. The absorbent structure of claim 10 wherein the content of synthetic matrix fibers in the top stratum of the upper ply is from about 75 to about 90% by weight.

13. The absorbent structure of claim 1 wherein the basis weight of the middle stratum of the upper ply is from about 80 gsm to about 300 gsm.

14. The absorbent structure of claim 1 wherein the content of superabsorbent polymer particles in the middle stratum of the upper ply is from about 5 to about 60% by weight of the upper ply.

15. The absorbent structure of claim 14 wherein the content of superabsorbent polymer particles in the middle stratum of the upper ply is from about 20 to about 50% by weight.

16. The absorbent structure of claim 1 wherein the bottom stratum of the upper ply is an airlaid layer.

17. The absorbent structure of claim 1 wherein the bottom stratum of the upper ply is a wet-laid cellulose tissue.

18. The absorbent structure of claim 1 wherein the apparent density of the lower ply is from about 0.15 g/cc to about 0.25 g/cc.

19. The absorbent structure of claim 1 wherein the basis weight of the lower ply is from about 150 gsm to about 400 gsm.

20. The absorbent structure of claim 1 wherein the content of superabsorbent polymer particles in the lower ply is from about 30 to about 80% by weight.

21. The absorbent structure of claim 20 wherein the content of superabsorbent polymer particles in the lower ply is from about 40 to about 60% by weight.

22. The absorbent structure of claim 1 wherein all layers of each ply are fully integrated in the forming process.

23. The absorbent structure of claim 1 wherein each ply is airlaid.

24. The structure of claim 1 wherein superabsorbent polymer particles are placed in at least one of the strata of the upper ply in longitudinal discrete lanes along the length of the core, said lanes including from about 70% to 100% superabsorbent polymer particles, and said lanes being separated by adjacent lanes including fibers and a binder.

25. The structure of claim 1 wherein superabsorbent polymer particles are placed in the lower ply in longitudinal discrete lanes along the length of the core, said lanes including from about 70% to 100% superabsorbent polymer particles, and said lanes being separated by adjacent lanes including fibers and a binder.

26. An absorbent structure having wet integrity higher than about 4.0 mN/gsm, softness higher than 8.0/J, pliability higher than about 70/N, and providing a substantially dry liquid-accepting surface after receiving a quantity of liquid, the said structure comprising:
   a) an upper ply having an upper fluid receiving surface and a lower surface comprising:
      i) a top stratum including synthetic matrix fibers bonded with a binder, said matrix fibers having length of from about 2 to about 15 mm;
      ii) a middle stratum in fluid communication with the top stratum, the middle stratum including natural fibers and superabsorbent polymer particles; and
      iii) a bottom stratum in fluid communication with the middle stratum, including natural fibers and a binder;
   b) and a lower ply in fluid communication with the upper ply, the lower ply having an upper surface and a lower surface and including:
      i) a top stratum including natural fibers and a binder; and
      ii) a bottom stratum including natural fibers, superabsorbent polymer particles, and a binder,
wherein:
   a) the lower surface of the upper ply has a surface area less than about 80% of the upper surface area of the lower ply;
   b) the top stratum of the upper ply exhibits essentially no fluid wicking capability;
   c) the basis weight of the top stratum of the upper ply is from about 20 gsm to about 120 gsm;
   d) the binder content (per cent by weight) of the top stratum of the upper ply is from about 5% to about 20%;
   e) the basis weight of the middle stratum of the upper ply is from about 50 gsm to about 1000 gsm;
   f) the binder content (per cent by weight) of the middle stratum of the upper ply is from about 1% to about 10%;
   g) the basis weight of the bottom stratum of the upper ply is from about 10 gsm to about 150 gsm;
   h) the binder content (per cent by weight) of the bottom stratum of the upper ply is from about 5% to about 15%;
   i) the content of superabsorbent particles in the upper ply is lower than the content of superabsorbent particles in the lower ply;
   j) the lower ply contains at least 30% superabsorbent particles based on the total basis weight of the lower ply;
   k) the top stratum of the lower ply contains from about 0% to about 20% superabsorbent particles based on the basis weight of the top stratum of the lower ply;
   l) the basis weight of the lower ply is from about 100 gsm to about 1000 gsm;
   m) the apparent density of the lower ply is about 0.15 g/cc to about 0.25 g/cc;
   n) the apparent density of the upper ply is lower than the apparent density of the lower ply; and
   o) the binder content (per cent by weight) of the lower ply is from about 1% to about 8%.

27. The absorbent structure of claim 26 wherein the length of the synthetic matrix fibers is from about 4 to about 12 mm.

28. The absorbent structure of claim 26 wherein the synthetic matrix fibers are from about 2 to about 30 denier.

29. The absorbent structure of claim 28 wherein the synthetic matrix fibers are from about 6 to about 15 denier.

30. The absorbent structure of claim 26 wherein the synthetic matrix fibers are selected from the group consisting of polyethylene, polypropylene, polyester, polyamide, cellulose acetate, rayon, and mixtures thereof.

31. The absorbent structure of claim 26 wherein the binder is selected from the group consisting of latex binders, thermoplastic powders, thermoplastic fibers, bicomponent fibers and mixtures thereof.

32. The absorbent structure of claim 26 wherein the binder is a water-soluble or water-dispersable bonding polymer agent.

33. The absorbent structure of claim 26 wherein the natural fibers are selected from the group consisting of cotton, softwood pulp, hardwood pulp, straw, keaf fibers, cellulose fibers modified by chemical, mechanical and/or thermal treatments, keratin and mixtures thereof.

34. The absorbent structure of claim 26 wherein the basis weight of the top stratum of the upper ply is from about 30 gsm to about 60 gsm.

35. The absorbent structure of claim 26 wherein the content of synthetic matrix fibers in the top stratum of the upper ply is from about 50 to about 99% by weight.

36. The absorbent structure of claim 26 wherein the content of synthetic matrix fibers in the top stratum of the upper ply is from about 75 to about 90% by weight.

37. The absorbent structure of claim 26 wherein the basis weight of the middle stratum of the upper ply is from about 80 gsm to about 300 gsm.

38. The absorbent structure of claim 26 wherein the content of superabsorbent polymer particles in the middle stratum of the upper ply is from about 5 to about 60% by weight of the upper ply.

39. The absorbent structure of claim 26 wherein the content of superabsorbent polymer particles in the middle stratum of the upper ply is from about 20 to about 50% by weight of the upper ply.

40. The absorbent structure of claim 26 wherein the basis weight of the lower ply is from about 150 gsm to about 400 gsm.

41. The absorbent structure of claim 26 wherein the overall content of superabsorbent polymer particles in the lower ply is from about 30 to about 80% by weight.

42. The absorbent structure of claim 26 wherein the content of superabsorbent polymer particles in the lower ply is from about 40 to about 60% by weight.

43. The absorbent structure of claim 26 wherein the bottom stratum of the upper ply is airlaid.

44. The absorbent structure of claim 26 wherein the bottom stratum of the upper ply is a wet-laid cellulose tissue.

45. The absorbent structure of claim 26 wherein the basis weight of the top stratum of the lower ply is from about 10 gsm to about 150 gsm.

46. The absorbent structure of claim 26 wherein the basis weight of the top stratum of the lower ply is from about 15 gsm to about 90 gsm.

47. The absorbent structure of claim 26 wherein all strata in each ply are fully integrated in the forming process.

48. The structure of claim 26 made by airlaid process.

49. The structure of claim 26 wherein superabsorbent polymer particles are placed in at least one of the strata of the upper ply in longitudinal discrete lanes along the length of the core, said lanes including from about 70% to 100% superabsorbent polymer particles, and said lanes being separated by adjacent lanes including fibers and a binder.

50. The structure of claim 26 wherein superabsorbent polymer particles are placed in at least in one stratum of the lower ply in longitudinal discrete lanes along the length of the core, said lanes including from about 70% to 100% superabsorbent polymer particles, and said lanes being separated by adjacent lanes including fibers and a binder.

51. An absorbent structure comprising:
a) an upper ply including:
   i) a top stratum including polyester matrix fibers bonded with latex in an amount of 15 to 25% by weight of said top stratum, said matrix fibers having length from about 4 mm to about 8 mm and having thickness from about 9 to about 15 denier per fiber, the basis weight of said top stratum being from about 40 to about 60 gsm;
   ii) a middle stratum in fluid communication with the top stratum, the middle stratum including softwood fluff, superabsorbent polymer particles, and binder fiber, the content of the superabsorbent polymer particles being from about 30 to 40% of the basis weight of the said middle stratum, the content of the binder fibers being from about 6 to about 12% of the basis weight of the said middle stratum, and the basis weight of the said middle stratum being from about 150 to about 200 gsm;
   iii) a bottom stratum in fluid communication with the middle stratum, including softwood fluff and binder fibers, the content of the binder fibers being from about 8 to about 16% of the basis weight of the said bottom stratum, and the basis weight of the said bottom stratum being from about 60 to about 120 gsm; and
b) a lower ply in fluid communication with the upper ply, the lower ply comprising:
   i) a top stratum including softwood fluff and binder fibers, the content of the binder fibers being from about 10 to about 25% of the basis weight of the said top stratum, and basis weight being from about 20 to about 60 gsm;
   ii) a bottom stratum including softwood fluff, superabsorbent polymer particles, and binder fibers, the content of the superabsorbent polymer particles being from about 50 to about 80% of the basis weight of the said bottom stratum, the content of the binder fibers being from about 2 to 5% of the basis weight of the said bottom stratum; and
   iii) cellulose tissue upon which the lower ply has been formed,
wherein:
a) the upper ply is airlaid and has a surface area adjacent to the lower ply, said surface area being from about 40 to 60% of the facing surface area of the lower ply;
b) the density of the upper ply is from about 0.05 to about 1.0 g/cc;
c) the density of the lower ply is from about 0.15 to about 0.3 g/cc.

52. An absorbent structure comprising:
a) an upper ply containing:
   i) a top stratum including polyester matrix fibers bonded with latex in an amount of 15 to 25% by weight of said top stratum, said matrix fibers having length from about 4 mm to about 8 mm and having thickness from about 9 to about 15 denier per fiber, the basis weight of said top stratum being from about 40 to about 60 gsm;
   ii) a middle stratum in fluid communication with the top stratum, the middle stratum including softwood fluff, superabsorbent polymer particles, and binder fiber, the content of the superabsorbent polymer particles being from about 40 to 60% of the basis weight of the said middle stratum, the content of the binder fibers being from about 6 to about 12% of the basis weight of the said middle stratum, and the basis weight of the said middle stratum being from about 200 to about 280 gsm;
   iii) a bottom stratum in fluid communication with the middle stratum, including softwood fluff and binder fibers, the content of the binder fibers being from about 8 to about 16% of the basis weight of the said bottom stratum, and the basis weight of the said bottom stratum being from about 60 to about 120 gsm; and
b) a lower ply in fluid communication with the upper ply, the lower ply comprising:
   i) a top stratum including softwood fluff and binder fibers, the content of the binder fibers being from about 10 to about 25% of the basis weight of the said top stratum, and basis weight being from about 20 to about 60 gsm;
   ii) a bottom stratum including softwood fluff, superabsorbent polymer particles, and binder fibers, the content of the superabsorbent polymer particles being from about 40 to about 60% of the basis weight of the said bottom stratum, the content of the binder fibers being from about 2 to 5% of the basis weight of the said bottom stratum, and the basis weight of the said bottom stratum being from about 200 to about 350 gsm; and
   iii) cellulose tissue upon which the lower ply has been formed,
wherein:
c) the upper ply is airlaid and has a surface area adjacent to the lower ply, said surface area being from about 40 to 60% of the facing surface area of the lower ply;
d) the density of the upper ply is from about 0.05 to about 1.0 g/cc;
e) the density of the lower ply is from about 0.15 to about 0.3 g/cc.

53. An absorbent article for absorbing body fluids, comprising the absorbent structure of claim 1 sandwiched between a liquid pervious topsheet and liquid impervious backsheet.

54. An absorbent article for absorbing body fluids, comprising the absorbent structure of claim 26 sandwiched between a liquid pervious topsheet and liquid impervious backsheet.

55. An absorbent article for absorbing body fluids, comprising the absorbent structure of claim 51 sandwiched between a liquid pervious topsheet and liquid impervious backsheet.

56. An absorbent article for absorbing body fluids, comprising the absorbent structure of claim 52 sandwiched between a liquid pervious topsheet and liquid impervious backsheet.

57. An absorbent structure having wet integrity higher than about 6.0 kN/gsm, softness higher than 8.0/J, pliability higher than about 70/N, and providing a substantially dry liquid-accepting surface after receiving a quantity of liquid, said structure comprising:
c) a top stratum comprising synthetic matrix fibers bonded with a binder, said matrix fibers having length from about 2 to about 15 mm;
d) a middle stratum in fluid communication with the top stratum, the middle stratum comprising natural fibers, superabsorbent polymer particles and a binder; and
e) a bottom stratum in fluid communication with the middle stratum, comprising natural fibers and a binder.

58. The absorbent structure of claim 57 wherein the synthetic matrix fibers are from about 2 to about 30 denier per fiber.

59. The absorbent structure of claim 58 wherein the synthetic matrix fibers are from about 6 to about 15 denier per fiber.

60. The absorbent structure of claim 57 wherein the synthetic matrix fiber is selected from the group consisting of polyethylene, polypropylene, polyester, polyamide, cellulose acetate, rayon fibers and mixtures thereof.

61. The absorbent structure of claim 57 wherein the binder is selected from the group consisting of latex binders, thermoplastic powders, thermoplastic fibers, bicomponent fibers and mixtures thereof.

62. The absorbent structure of claim 57 wherein the binder is selected from the group consisting of polyamide-polyamine epichlorohydrine adducts, cationic starch, dialdehyde starch, poly(vinyl alcohol), chitosan and mixtures thereof.

63. The absorbent structure of claim 57 wherein the natural fibers are selected from the group consisting of cotton, softwood pulps, hardwood pulps, straw, keaf fibers, cellulose fibers modified by chemical, mechanical and/or thermal treatments, keratin fibers and mixtures thereof.

64. The absorbent structure of claim 57 wherein the basis weight of the top stratum is from about 20 gsm to about 120 gsm.

65. The absorbent structure of claim 64 wherein the basis weight of the top stratum is from about 30 gsm to about 60 gsm.

66. The absorbent structure of claim 57 wherein the content of synthetic matrix fibers in the top stratum is from about 50 to about 99% by weight.

67. The absorbent structure of claim 66 wherein the content of synthetic matrix fibers in the top stratum is from about 75 to about 90% by weight.

68. The absorbent structure of claim 57 wherein the basis weight of the middle stratum is from about 50 gsm to about 1000 gsm.

69. The absorbent structure of claim 68 wherein the basis weight of the middle stratum of the upper ply is from about 80 gsm to about 300 gsm.

70. The absorbent structure of claim 57 wherein the content of superabsorbent polymer particles in the middle stratum is from about 5 to about 60% by weight of the absorbent structure.

71. The absorbent structure of claim 70 wherein the content of superabsorbent polymer particles in the middle stratum is from about 20 to about 50% by weight.

72. The absorbent structure of claim 57 wherein the bottom stratum is an airlaid layer.

73. The absorbent structure of claim 57 wherein the bottom stratum is a wet-laid cellulose tissue.

74. The absorbent structure of claim 57 wherein all strata of the said structure are fully integrated in the forming process.

75. The absorbent structure of claim 57 made by airlaid process.

76. The structure of claim 57 wherein superabsorbent polymer particles are placed at least in one of the strata in longitudinal discrete lanes along the length of the core, said lanes including from about 70% to 100% superabsorbent polymer particles, and said lanes being separated by adjacent lanes including fibers and a binder.

77. An absorbent structure, comprising:
i. a top stratum comprising polyester fibers bonded with latex in an amount of 15 to 25% by weight of said top stratum, said matrix fibers having length from about 4 mm to about 8 mm and having thickness from about 9 to about 15 denier per fiber, the basis weight of said top stratum being from about 40 to about 60 gsm;
ii. a middle stratum in fluid communication with the top stratum, the middle stratum comprising softwood fluff fiber, superabsorbent polymer particles, and binder fiber, the content of the superabsorbent polymer particles being from about 30 to 40% of the basis weight of the said middle stratum, the content of the binder fibers being from about 6 to about 12% of the basis weight of the said middle stratum, and the basis weight of the said middle stratum being from about 150 to about 200 gsm; and
iii. a bottom stratum in fluid communication with the middle stratum, comprising softwood fluff and binder fibers, the content of the binder fibers being from about 8 to about 16% of the basis weight of the said bottom stratum, and the basis weight of the said bottom stratum being from about 60 to about 120 gsm,
wherein the density of the structure is from about 0.05 to about 0.3 g/cc, and the structure has a wet integrity higher than about 6.0 mN/gsm, softness higher than 8.0/J and pliability higher than about 70/N.

78. An absorbent structure, comprising:
i. a top stratum comprising polyester matrix fibers bonded with latex in an amount of 15 to 25% by weight of said top stratum, said matrix fibers having length from about 4 mm to about 8 mm and having thickness from about 9 to about 15 denier per fiber, the basis weight of said top stratum being from about 40 to about 60 gsm;
ii. a middle stratum in fluid communication with the top stratum, the middle stratum comprising softwood fluff fiber, superabsorbent polymer particles, and binder fiber, the content of the superabsorbent polymer particles being from about 40 to 60% of the basis weight of the said middle stratum, the content of the binder fibers being from about 6 to about 12% of the basis weight of the said middle stratum, and the basis weight of the said middle stratum being from about 200 to about 280 gsm; and
iii. a bottom stratum in fluid communication with the middle stratum, comprising softwood fluff and binder fibers, the content of the binder fibers being from about 8 to about 16% of the basis weight of the said bottom stratum, and the basis weight of the said bottom stratum being from about 60 to about 120 gsm,
wherein the density of the said structure is from about 0.05 to about 1.0 g/cc, and the structure has a wet integrity higher than about 6.0 mN/gsm, softness higher than 8.0/J and pliability higher than about 70/N.

79. An absorbent article for absorbing body fluids, comprising the absorbent structure of claim 57 sandwiched between a liquid pervious topsheet and liquid impervious backsheet.

* * * * *